United States Patent [19]

Suami

[11] 4,452,814
[45] Jun. 5, 1984

[54] NITROSOUREA DERIVATIVES

[76] Inventor: Tetsuo Suami, 5-8, Nakamachi 3-chome, Musashino-shi, Tokyo, Japan

[21] Appl. No.: 338,923

[22] Filed: Jan. 12, 1982

[30] Foreign Application Priority Data

Jan. 12, 1981 [JP] Japan .................................. 56-2135

[51] Int. Cl.³ .................... A61K 31/17; C07C 127/16
[52] U.S. Cl. ........................................ 424/322; 564/33
[58] Field of Search .......................... 564/33; 424/322

[56] References Cited

U.S. PATENT DOCUMENTS

| | | | |
|---|---|---|---|
| 3,859,277 | 1/1975 | Marakami et al. ..................... | 564/33 |
| 4,010,281 | 3/1977 | Yomada et al. ....................... | 564/48 |
| 4,028,410 | 6/1977 | Yanko et al. .......................... | 564/33 |
| 4,039,578 | 8/1977 | Suami ................................... | 564/33 |
| 4,148,921 | 4/1979 | Suami ................................... | 564/33 |
| 4,335,247 | 6/1982 | Takatori et al. ...................... | 564/33 |

OTHER PUBLICATIONS

Zeller et al., "Chemotherapeutic Activity of 2-Chloroethylnitrosocarbamoyl Derivatives of Amino Acids in a Transplanted Rat Leukemia" (L5222) Drug Res. 32(I) 1982.

Tang et al., "Synthesis of Potentially Antineoplastic Derivatives of N-[N-(2-Cloroethyl)-N-Nitrosocarbamoyl]Amino Acids" Arch. Pharm., vol. 314, 1981.

Torrence et al. "5-Substituted Uracil Arabinonucleosides as Potential Antiviral Agents", J. of Med. Chem., 1979, vol. 22, No. 3.

Primary Examiner—Donald B. Moyer
Assistant Examiner—C. Joseph Faraci

Attorney, Agent, or Firm—Sughrue, Mion, Zinn, Macpeak and Seas

[57] ABSTRACT

Nitrosourea derivatives are provided which possess a high level of inhibitory activity against leukemia and tumors and which are therefore useful for pharmaceutical purposes. The compounds have the structure represented by formulae (I), (II) and (III):

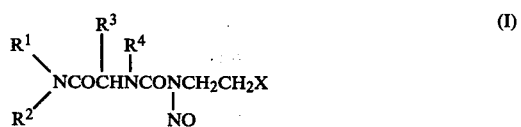

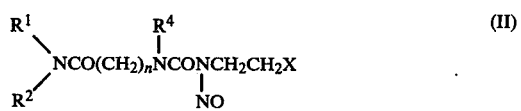

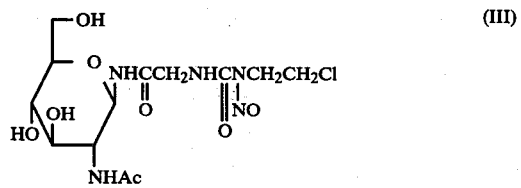

wherein $R^1$, $R^2$ and $R^4$ may be the same or different and each represent a hydrogen atom or an alkyl, aryl, aralkyl, alkanoyl or a heterocyclic group; $R^3$ represents the residual group on the α-carbon atom of an α-amino acid; n represents 2 or 3; X represents a halogen atom selected from chlorine, fluorine and bromine; and Ac represents an alkanoyl group.

4 Claims, No Drawings

NITROSOUREA DERIVATIVES

BACKGROUND OF THE INVENTION

This invention relates to novel nitrosourea derivatives which exhibit a high level of inhibitory activity against leukemia and tumors, to a process for the preparation thereof and to their use for pharmaceutical purposes.

There are a variety of compounds which have been proposed as being effective for inhibiting leukemia and tumors, one class of which is nitrosourea derivatives. Among the nitrosourea derivatives, streptozotocin [N-(N'-methyl-N'-nitrosocarbamoyl)-D-glucosamine] and its derivatives such as methyl glucosaminides are typical ones early developed (refer to U.S. Pat. No. 3,577,406 and U.S. Pat. No. 3,767,640, for example), but they are not satisfactory yet because of insufficient activity against leukemia and tumors and/or undesirable side effects thereof. Another class of nitrosourea derivatives is haloalkylnitrosoureas, a typical example of which is 1,3-bis(2-chloroethyl)-1-nirosourea (abbreviated as BCNU) [refer to, for example A. Goldin et al., Cancer Chemotherapy Rept., 40, 57 (1964) and T. P. Johnston et al., Journal of Medicinal Chemistry 9, 892~911 (1966)].

I have also investigated on the synthesis and chemical and pharmacological properties of some wide range of nitrosoureas and recently proposed, as highly interesting series of those compouns, glycosyl derivatives of nitrosoureas (refer to T. Suami et al., U.S. Pat. No. 4,086,415, U.S. Pat. No. 4,157,439 and U.S. Pat. No. 4,220,643) and hydroxy-substituted cyclohexyl derivatives of nitrosoureas (refer to T. Suami et al., U.S. Pat. No. 4,180,655). The most interesting compound of the former series is 1-(2-chloroethyl)-3-(β-D-glucopyranosyl)-1-nitrosourea (abbreviated as GANU) and that of the latter series is 1-(2-chloroethyl)-3-(1,3/2N-dihydroxycyclohexyl)-1-nitrosourea (abbreviated as DONU), both of which have a broad spectrum of antitumor activity against a wide variety of experimental leukemia and tumors with positive expectation of the efficacy in human cancer chemotherapy.

BRIEF SUMMARY OF THE INVENTION

I have now found, as a result of my continuing investigations, new, three series of nitrosourea derivatives which also possess a high inhibitory activity against leukemia and tumors with a low toxicity as corroborated by in vivo tests.

According to a first aspect of this invention, therefore, there are provided as the first series of new compounds nitrosourea derivatives of formula (I):

(I)

wherein $R^1$, $R^2$ and $R^4$ may be the same or different and each represent a hydrogen atom or an alkyl, aryl, aralkyl, alkanoyl or a heterocyclic group; $R^3$ represents the residual group on the α-carbon atom of an α-amino acid; and X represents a halogen atom selected from chlorine, fluorine and bromine.

In the definition of $R^3$ above, the words "the residual group on the α-carbon atom of an α-amino acid" mean a group which forms an α-amino acid when attached to a carbon atom to which an amino group, a carboxyl group and a hydrogen atom have been attached. Thus, the group

means such residual moiety of an α-amino acid that will occur or be derived when the α-amino group and the α-carboxyl group are removed from the molecule of the α-amino acid. For example, the group

may be of the formula:

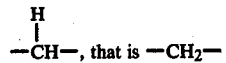

which is derived from glycine by the removal of the amino and carboxyl groups from glycine molecule, or of the formula

which is derived from alanine in the same manner, or of the formula:

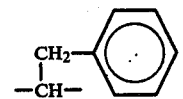

which is derived from phenylalanine similarly, or of the formula:

which is derived from serine, or of the formula:

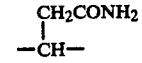

which is derived from asparagine, and so on. Typical examples of such residual group $R^3$ are those on the α-carbon atom of glycine, alanine, phenylalanine, sarcosine, serine, tryptophan, proline, methionine, cysteine, tyrosine, valine, leucine, isoleucine, threonine, aspartic acid, asparagine, glutamic acid, glutamine, lysine, hydroxylysine, histidine and arginine.

According to a second aspect of this invention, there are provided as the second series of new compounds nitrosourea derivatives of formula (II):

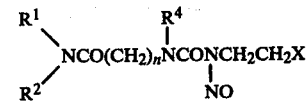
(II)

wherein $R^1$, $R^2$, $R^4$ and X have the same meanings as defined above and n represents 2 or 3.

According to a third aspect of this invention, there are provided as the third series of new compounds nitrosourea derivatives of formula (III):

wherein Ac represents an alkanoyl group.

DETAILED DESCRIPTION OF THE INVENTION

In formulae (I) and (II) above, $R^1$, $R^2$ and $R^4$ each are preferably a lower alkyl group having 1~4 carbon atoms such as methyl, ethyl, propyl and butyl; a phenyl group unsubstituted or substituted with a lower alkyl (particularly methyl), a lower alkoxy (particularly methoxy) or a halogen (particularly chlorine); an aralkyl group containing 1~4 carbon atoms in the alkyl moiety thereof, particularly phenylalkyl containing 1~4 carbon atoms in the alkyl moiety thereof; a lower alkanoyl group containing 1~4 carbon atoms in the alkyl moiety thereof (particularly acetyl); and furyl, thienyl, pyridyl, pyrimidyl, imidazolyl and acridinyl groups and the like.

According to this invention, the nitrosourea derivatives of formula (I) may be prepared through two different routes. Thus, the first process comprises reacting a compound of formula (IV):

wherein $R^1$, $R^2$, $R^3$ and $R^4$ have the same meanings as defined above with p-nitrophenyl N-(2-haloethyl)-N-nitrosocarbamate at a temperature of 0° C. to 50° C. in a suitable solvent such as tetrahydrofuran.

The second process comprises reacting a compound of formula (V):

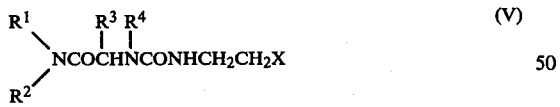

wherein $R^1$, $R^2$, $R^3$, $R^4$ and X have the same meanings as defined above with a nitrosating agent in a suitable solvent. Any conventional nitrosating agent such as sodium nitrite, nitrogen trioxide, nitrogen tetroxide, nitrosyl chloride and the like may be used. Examples of solvent to be used for this reaction are organic solvents such as formic acid, acetic acid and the like. Reaction temperature may usually be 0° C.~80° C.

The object compound of formula (I) so produced in either of the two processes above may easily be separated from the reaction solution and purified in a conventional manner per se including a treatment with an ion exchange resin, a column chromatography and a recrystallization with an organic solvent.

The nitrosourea derivatives of formula (II) may be prepared, according to this invention, in the same manner as that used in the preparation of the compounds of formula (I). Thus, both the first and second processes above-mentioned for the compounds of formula (I) are applicable similarly to the preparation of the compounds of formula (II), provided that the starting compounds of formulae (IV) and (V) are replaced by compounds of formulae (VI) and (VII):

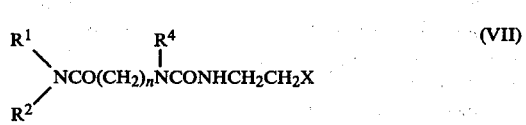

wherein $R^1$, $R^2$, $R^4$, X and n have the same meanings as defined above, respectively, in the first and second processes.

In formula (III) above, Ac is preferably a lower alkanoyl group containing 1~4 carbon atoms in the alkyl moiety thereof, particularly acetyl group.

The nitrosourea derivatives of formula (III) may be prepared, according to this invention, through the following route:

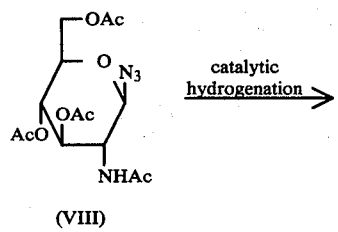

(VIII)

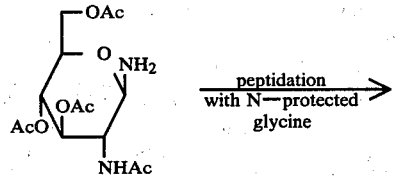

(IX)

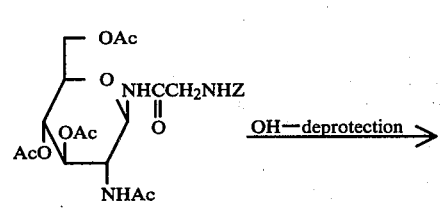

(X)

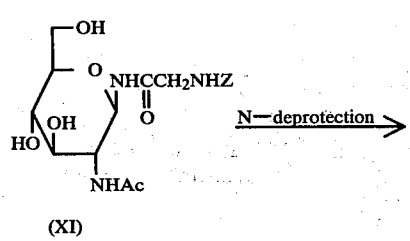

(XI)

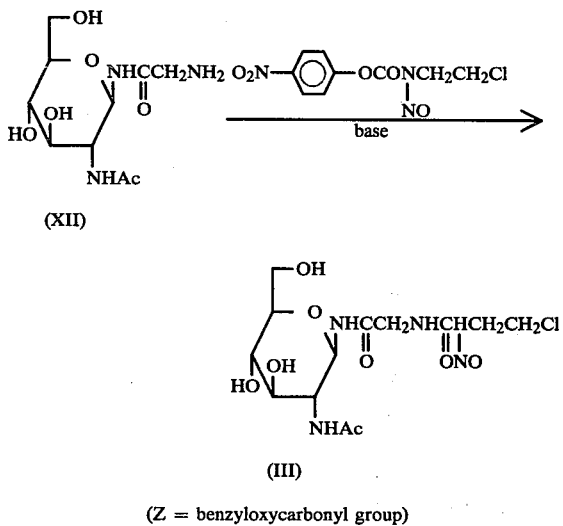

(Z = benzyloxycarbonyl group)

The catalytic hydrogenation of azide derivative (VIII) to amino derivative (IX) may be carried out in a conventional manner, for example in the presence of Raney nickel catalyst in methanol.

In the subsequent peptidation of amino derivative (IX), the N-protected glycine may preferably be used in the form of an active ester which is prepared by reacting the N-protected glycine with N-hydroxysuccinimide in the presence of dicyclohexylcarbodiimide (DCC) in a suitable solvent in a known manner. The peptidation is effected by reacting amino derivative (IX) with the active ester at a temperature of 0° C.~50° C. in the presence of a base such as triethylamine, N,N-dimethylamine and monoethylamine in a suitable solvent such as dimethylformamide, methanol, ethanol and dioxane to yield compound (X).

The deprotection of the OH group of compound (X) may be carried out in a usual manner, for example by reacting the compound with sodium methoxide in a suitable solvent. Subsequently, the deprotection of the N-protecting group Z(benzyloxycarbonyl group) of compound (XI) so produced may be carried out in a usual manner, for example by a catalytic hydrogenation in the presence of palladium black to yield compound (XII).

The final peptidation step may be achieved by reacting compound (XII) with p-nitrophenyl N-(2-chloroethyl)-N-nitrosocarbamate at a temperature of 0° C.~50° C. in the presence of a base such as triethylamine in a suitable solent such as tetrahydrofuran to afford compound (III).

The isolation of compound (III) from the reaction solution and the purification thereof may be carried out in a similar way to that mentioned above for those purposes of compounds (I) and (II).

Typical examples of the nitrosourea derivatives of formula (I) may include:
N-[N'-(2-chloroethyl)-N'-nitrosocarbamoyl]glycine amide;
N-[N'-(2-chloroethyl)-N'-nitrosocarbamoyl]sarcosine amide;
N-[N'-(2-chloroethyl)-N'-nitrosocarbamoyl]-L-phenylalanine amide;
N-[N'-(2-chloroethyl)-N'-nitrosocarbamoyl]-L-tyrosine amide;
N-[N'-(2-chloroethyl)-N'-nitrosocarbamoyl]-L-valine amide;
N-[N'-(2-chloroethyl)-N'-nitrosocarbamoyl]-DL-leucine amide;
N-[N'-(2-chloroethyl)-N'-nitrosocarbamoyl]-L-serine amide;
N-[N'-(2-chloroethyl)-N'-nitrosocarbamoyl]-L-methionine amide; and
N-[N'-(2-chloroethyl)-N'-nitrosocarbamoyl]-proline amide.

Typical examples of the nitrosourea derivatives of formula (II) may include:
N-[N'-(2-chloroethyl)-N'-nitrosocarbamoyl]-$\beta$-alanine amide; and
N-[N'-(2-chloroethyl)-N'-nitrosocarbamoyl]-$\gamma$-aminobutyric acid amide.

A typical example of the nitrosourea derivatives of formula (III) is 2-acetamide-1-[[[[(2-chloroethyl)nitroso-amino]carbonyl]glycyl]amino]-1,2-dideoxy-$\beta$-D-glucopyranose.

Antileukemic activity of a typical nitrosourea derivative of formula (I) according to this invention was tested on Leukemia L 1210 in mice, details of which are given below.

Compound

N-[N'-(2-chloroethyl)-N'-nitrosocarbamoyl]glycine amide

Animals

Male $BDF_1$ mice, aged about 7 weeks old and weighing 22±1 g were used in groups of five animals for each test.

Tumor cells

Leukemia L 1210 cells were inoculated intraperitoneally in a concentration of $1 \times 10^6$ cells/0.05 ml/mouse.

Method

The test compound was dissolved in a physiological salt solution to give a series of solutions in predetermined concentrations and 0.1 ml of the each solution was administered intraperitoneally to each mouse once a day from the 24th hour after the tumor cell inoculation for 3 consecutive days. The antileukemic activity of the test compound was assessed by mean survival days and percentage increase in life-span. The percentage increase in life-span (ILS) was calculated as follows:

$$ILS\ (\%) = \frac{T - C}{C} \times 100$$

T: The mean survival days of the treated animals
C: The mean survival days of the untreated animals The control test for this purpose was carried out in the same way as that used for the test compound except that 0.1 ml of the physiological salt solution was administered in place of the solution of the test compound.

The test results are shown in the following table.

| Dose of compound (mg/kg) | Mean survival days treated/control | ILS (%) |
|---|---|---|
| 16 | >60.0/7.7 | >679.2 |
| 8 | >60.0/7.7 | >679.2 |
| 2 | 14.0/7.7 | 81.8 |
| 1 | 10.6/7.7 | 37.7 |

| Dose of compound (mg/kg) | Mean survival days treated/control | ILS (%) |
| --- | --- | --- |
| 0.5 | 10.2/7.7 | 32.5 |

It will be clearly appreciated from the above test results that the novel nitrosourea derivatives according to this invention show a high value of ILS in a very low dose with zero volume of ascites and are therefore expected to be useful in human chemotherapy of leukemic and tumor diseases.

The nitrosourea derivatives of formulae (I), (II) and (III) according to this invention are further characterized by their low toxicity. Thus, acute toxicity represented by $LD_{50}$ of some typical compounds of formula (I), when administered intraperitoneally (i.p.) or intravenously (i.v.) to $BDF_1$ male mice aged about 6-weeks old and observed after the lapse of 21 days according to Litchfield-Wilcoxon's method, is as follows:

| Comound | $LD_{50}$ (mg/kg) | |
| --- | --- | --- |
| | i.p. | i.v. |
| N—[N'—(2-chloroethyl)-N'—nitrosocarbamoyl]glycine amide | 21.2 | 22.4 |
| N—[N'—(2-chloroethyl)-N'—nitrosocarbamoyl]sarcosine amide | 392.0 | 426.6 |
| N—[N'—(2-chloroethyl)-N'—nitrosocarbamoyl]proline amide | 219.6 | 195.4 |

According to a further aspect of this invention, therefore, there is provided a pharmaceutical composition comprising a therapeutically effective amount of a nitrosourea derivative of formula (I), (II) or (III) in association with a pharmaceutically acceptable excipient, carrier or diluent.

The pharmaceutical composition may be in a form known per se to suit the route of administration that is oral or injection administration for man or oral, injection of intraperitoneal administration for animals. In general, therefore, the pharmaceutical composition may take such form as an ampoule, capsule, tablet, powder, granule and the like to adapt it for oral or injection administration.

This invention also includes as a further aspect thereof a method for the therapeutic treatment of leukemia and tumor diseases in man and animals which comprises administering to the patient a therapeutically effective amount, at suitable intervals, of a nitrosourea derivative of formula (I), (II) or (III) above. It will be appreciated that the amount of the nitrosourea derivative to be actually applied will vary dependent upon the particular compound used, the particular composition formulated, the mode of application, the route of administration and other variables. Many factors which modify the action of the drug will be taken into account by those skilled in the art, for example, age, body weight, sex, diet, time of administration, route of administration, rate of metabolism or excretion, drug combination, sensitivity, and severity or condition of the disease. Optimal application dose for a given set of conditions can be ascertained by those skilled in the art using conventional tests for the dosage determination in view of the above guidelines.

The following Examples illustrate the preparation of the nitrosourea derivatives of this invention together with the preparation of the starting and intermediate compounds.

EXAMPLE 1

Preparation of N-[N'-(2-chloroethyl)-N'-nitrosocarbamoyl]glycine amide

Glycine amide hydrochloride (200 mg, 1.81 mmol.) was dissolved in water (10 ml). Amberlite IRA-400 ($OH^-$ form), a strongly basic anion exchange resin made and sold by Rohm & Haas Company, (5.4 ml) was added to the solution and the mixture was stirred for 15 minutes to cause dehydrochlorination.

After the resin was filtered off, the filtrate was concentrated in vacuo to leave an oily residue. The residue was dissolved in methanol (3 ml), to which was added dropwise a solution of p-nitrophenyl N-(2-chloroethyl)-N-nitrosocarbamate (520 mg, 1.05 moles per mole of the starting compound) in tetrahydrofuran (7 ml) in the dark under stirring. After the lapse of 30 minutes, the reaction solution was analyzed by TLC with a developer system of chloroform-methanol (5:1 by volume), when the formation of a condensation product giving a single spot at Rf 0.62 was confirmed. The reaction solution was then concentrated in vacuo to leave a deep yellow oily residue. The residue was purified by column chromatography on silica gel (Wako-gel C-300, 5 g, a product of Wako Pure Chemical Co., Ltd.) with a developer system of chloroform-ethanol (8:1 by volume), where the eluate from the silica gel column was collected in fractions and the fractions containing the desired product were combined together and concentrated in vacuo to leave a pale yellow oily residue (350 mg). The residue was crystallized from ethyl ether followed by washing with ethanol, thus yielding N-[N'-(2-chloroethyl)-N'-nitrosocarbamoyl]glycine amide (275 mg) as pale yellow prism-like crystals.

Yield: 72.9%; m.p. 125°-126° C. (Dec.)

Elemental analysis: Calculated for $C_5H_9N_4O_3Cl$, MW=208.611: C, 28.79, H, 4.35, N, 26.86, Cl, 17.00%. Found: C, 29.00, H, 4.35, N, 26.56, Cl, 17.35%.

EXAMPLE 2

Preparation of N-[N'-(2-chloroethyl)-N'-nitrosocarbamoyl]sarcosine amide

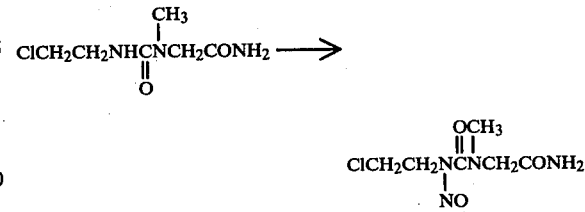

N-[N'-(2-Chloroethyl)carbamoyl]sarcosine amide (100 mg, 0.516 mmol.) was dissolved in a 99% formic acid (0.7 ml) under ice-cooling, to which sodium nitrite (53.4 mg, 1.5 moles per mole of the starting compound) was slowly added and the mixture was held under stirring for further 30 minutes to complete the reaction.

Then, Amberlite IR-120 (H+ form), a strongly acidic cation exchange resin made and sold by Rohm & Haas Company, (1 ml) and methanol (1 ml) were added to the resulting reaction solution and the mixture was stirred for 10 minutes. After the resin was removed by filtration, the reaction solution was concentrated in vacuo to leave an oily residue. The residue was purified by column chromatography on silica gel (Wako-gel C-300) with a developer system of toluene-ethanol (3:1 by volume), where the eluate was collected in fractions and the fractions containing the main product were collected together and concentrated in vacuo to afford N-[N'-(2-chloroethyl)-N'-nitrosocarbamoyl]sarcosine amide (62 mg) as a white crystalline residue.

Yield: 53.9%; m.p. 86°–88° C. (Dec.)

Elemental analysis: Calculated for $C_6H_{11}N_4O_3Cl$, MW=222.637: C, 32.37, H, 4.98, N, 25.17, Cl, 15.93%. Found: C, 32.14, H, 4.88, N, 24.81, Cl, 16.18%.

EXAMPLE 3

Preparation of 2-acetamido-1-[[[[(2-chloroethyl)nitroso-amino]carbonyl]gycyl]amino]-1,2-dideoxy-β-D-glucopyranose

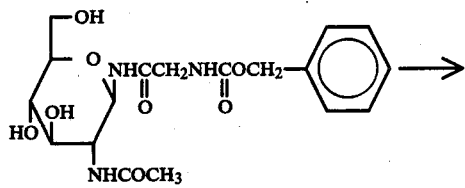

(XI)

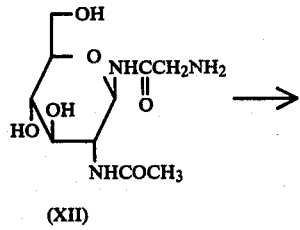

(XII)

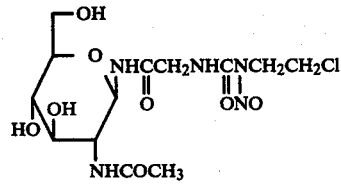

(III)

Compund (XI) (210 mg, 0.51 mmol.) which was prepared according to A. Yamamoto et al's process (Chem. Pharm. Bull. 13 (1965) 1036) was dissolved in methyl cellosolve (15 ml) and the solution was catalytically hydrogenated in the presence of Pd-black (25 mg) under the initial hydrogen pressure of 50 psi overnight to form the free amino compound (XII).

After the catalyst was removed by filtration, the reaction solution was concentrated in vacuo to leave a white jelly. The jelly was suspended in methanol (7 ml), to which triethylamine (25.8 mg, 0.5 moles per mole of the starting compound) was added and then a solution of p-nitrophenyl N-(2-chloroethyl)-N-nitrosocarbamate (419 mg, 3 moles per mole of the starting compound) in tetrahydrofuran (7 ml) was added dropwise over about 15 minutes under stirring in the dark. The mixture was held at room temperature under stirring for further 3 hours to complete the reaction, after which the reaction solution was analyzed by TLC with a developer system of chloroform-methanol (3:1 by volume) which confirmed the presence of a main spot at Rf 0.37 for the desired product having a UV absorption, a secondary spot at Rf 0.18 for a by-product and a slight spot at the origin for the starting compound. Then, the reaction solution was concentrated in vacuo at room temperature to leave a deep yellow oily residue which was then treated with methanol/isopropyl ether in a usual manner to leave a pale yellow solid residue. The residue was purified by column chromatography on silica gel (Wako gel C-300, 10 g) with a developer system of chloroform-ethanol (8:1 by volume) and then with a developer system of chloroform-methanol (4:1 by volume) wherein the charging was with chloroform-methanol (2:1 by volume). Fractions corresponding to $R_f=0.37$ with a UV absorption were collected together, concentrated in vacuo and solidified from acetone-ethyl acetate to yield the desired compound (III) (96 mg).

Yield: 45.7%; m.p. 122° C.

Specific rotation $[\alpha]_D^{20}+34.5°$ (c 0.4, methanol);

Elementary analysis: Calculated for $C_{13}H_{22}N_5O_3Cl$; MW=411.803: C, 37.91, H, 5.39, N, 17.01, Cl, 8.61%. Found: C, 37,88, H, 5.72, N, 16.62, Cl, 8.23%.

EXAMPLE 4

Preparation of N-[N'-(2-chloroethyl)-N'-nitrosocarbamoyl]-β-alanine amide (1) N-Benzyloxycarbonyl-β-alanine amide

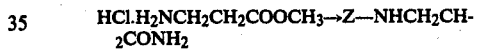

(Z=benzyloxycarbonyl group)

β-Alanine methyl ester hydrochloride (1.00 g, 7.16 mmol.) was dissolved in water (3.5 ml), to which were added chloroform (40 ml) and a 33% solution of benzyloxycarbonyl chloride in toluene (4.5 ml) and then added dropwise a 2 N aqueous sodium carbonate solution (16.5 ml) under a vigorous stirring and ice-cooling. The resulting mixture was held for further 30 minutes under the same conditions as above and then held at room temperature for 30 minutes to complete the reaction.

The reaction mixture was allowed to stand to separate layers. The aqueous layer was washed with chloroform (10 ml×2). All the chloroform layers separated were combined together and dried with anhydrous sodium sulfate. After the sodium sulfate was removed, the chloroform extract was concentrated and dried in vacuo to afford methyl N-benzyloxycarbonyl-β-alaninate in the form of an oily residue. The residue was dissolved in an ammonia gas-saturated methanol (20 ml) at 0° C. and the resulting solution was allowed to stand at room temperature for 5 days under a sealed condition.

The reaction solution was then analyzed by TLC with a developer system of benzene-ethanol (9:1 by volume), where it was confirmed that the spot at Rf 0.48 for methyl N-benzyloxycarbonyl-β-alaninate disappeared and that a main spot at Rf 0.14 for the object compound and a secondary spot at Rf 0.35 for a small amount of a by-product appeared. The deposited small prism-like crystals were separated by filtration as the titled compound (795 mg). The filtrate was concentrated and then stored in a refrigerator, thus yielding a further amount (494 mg) of the titled compound as secondary crystals.

Total yield: 1.289 g; Yield: 81.0%; m.p. 164°–165° C.;

Elementary analysis: Calculated for $C_{11}H_{14}N_2O_3$, MW=222.238: C, 59.45, H, 6.35, N, 12.61%. Found: C, 59.67, H, 6.41, N, 12.44%.

(2) N-[N'-(2-Chloroethyl)-N'-nitrosocarbamoyl]-β-alanine amide

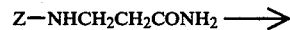

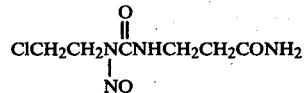

The compound obtained in step (1) above (300 mg, 1.35 mmol.) was dissolved in methyl cellosolve (10 ml) and the solution was catalytically hydrogenated in the presence of Pd-black (30 mg) under the initial hydrogen pressure of 50 psi overnight.

After the catalyst was removed by filtration, the filtrate was concentrated in vacuo to leave an oily residue. The residue was dissolved in methanol (3 ml), to which triethyl amine (68 mg) was added and then a solution of p-nitrophenyl N-(2-chloroethyl)-N-nitrosocarbamate (443 mg, 1.2 moles per mole of the starting compound) in tetrahydrofuran (5 ml) was added dropwise over about 5 minutes under stirring in the dark. The mixture was held at room temperature under stirring for further 60 minutes to complete the reaction. The reaction solution was then analyzed by TLC with a developer system of chloroform-methanol (7:1 by volume), where it was confirmed that a substantially single compound was formed with a spot at $R_f$ 0.40 which showed a UV absorption.

The reaction solution was concentrated in vacuo to leave a deep yellow oily residue. The residue was purified by column chromatography on silica gel (Wako-gel C-300, 15 g) with a developer system of chloroform-ethanol (8:1 by volume). Fractions containing the desired object product were collected together and concentrated in vacuo to leave a pale yellow oily residue. The residue was crystallized from ethyl ether, affording the titled compound (176 mg).

Yield: 58.6%; m.p. 95°–97° C. (Dec.);

Elementary analysis: Calculated for $C_6H_{11}N_4O_3Cl$, MW=222.637; C, 32.37, H, 4.98, N, 25.17, Cl 15.93%. Found: C, 32.14, H, 4.96, N, 24.95, Cl 16.07%.

EXAMPLE 5

Preparation of N-[N'-(2-chloroethyl)-N'-nitrosocarbamoyl]-γ-aminobutyric acid amide (1) N-Benzyloxycarbonyl-γ-aminobutyric acid amide HCl.H₂NCH₂CH₂CH₂COOCH₃→Z-NHCH₂CH₂CH₂CONH₂

Methyl γ-aminobutyrate hydrochloride (1.5 g, 9.76 mmol.) was subjected to benzyloxycarbonylation in the same manner as in Example 4 (1) to yield methyl N-benzyloxycarbonyl-γ-aminobutyrate as an oily residue. The residue was dissolved in an ammonia gas-saturated methanol (30 ml) at 0° C. and the solution was allowed to stand at room temperature for 5 days under a sealed condition.

The reaction solution was then analyzed by TLC with a developer system of benzene-ethanol (9:1 by volume), where it was confirmed that the spot at $R_f$ 0.50 for methyl N-benzyloxycarbonyl-γ-aminobutyrate disappeared and that a main spot at $R_f$ 0.12 for the object product and a secondary spot at $R_f$ 0.39 for a small amount of a by-product appeared.

The reaction solution was concentrated in vacuo to leave a white crystalline residue to which a small amount of methanol was added and the whole was filtered to yield the titled compound (1.45 g).

Yield: 62.9%; m.p. 128°–130° C.;

Elemental analysis: Calculated for $C_{12}H_{16}N_2O_3$, MW=236.264: C, 61.00, H, 6.83, N, 11.86%. Found: C, 61.43, H, 7.10, N, 11.73%.

(2) N-[N'-(2-Chloroethyl)-N'-nitrosocarbamoyl]-γ-aminobutyric acid amide

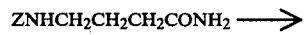

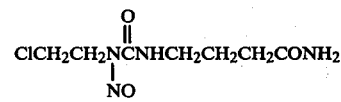

The compound obtained in step (1) above (300 mg, 1.27 mmol.) was dissolved in methyl cellosolve (10 ml) and the solution was catalytically hydrogenated in the presence of Pd-black (30 mg) under the initial hydrogen pressure of 50 psi overnight.

After the catalyst was removed by filtration, the filtrate was concentrated in vacuo to leave an oily residue. The residue was dissolved in methanol (3 ml), to which triethyl amine (64 mg, 0.5 moles per mole of the starting compound) was added and then a solution of p-nitrophenyl N-(2-chloroethyl)-N-nitrosocarbamate (417 mg, 1.2 moles per mole of the starting compound) in tetrahydrofuran (5 ml) was added dropwise over about 5 minutes under stirring in the dark. The mixture was held at room temperature under stirring for further 60 minutes to complete the reaction. The reaction solution was then analyzed by TLC with a developer system of chloroform-methanol (7:1 by volume), where it was confirmed that a substantially single compound was formed with a spot at $R_f$ 0.39 which showed a UV absorption.

The reaction solution was concentrated in vacuo to leave a deep yellow oily residue. The residue was purified by column chromatography on silica gel (Wako-gel C-300, 15 g) with a developer system of chloroform-ethanol (8:1 by volume). Fractions containing the desired object product were collected together and concentrated in vacuo to leave a pale yellow crystalline solid residue. The residue was washed with ethyl ether, affording the titled compound (190 mg).

Yield: 63.2%; m.p. 102°–103.5° C. (Dec.);

Elemental analysis: Calculated for $C_7H_{13}N_4O_3Cl$, MW=236.663: C, 35.52, H, 5.54, N, 23.68, Cl, 14.98%. Found: C, 35.83, H, 5.58, N, 23.82, Cl, 14.65%.

EXAMPLE 6

Preparation of
N-[N'-(2-chloroethyl)-N'-nitrosocarbamoyl]-L-phenylalanine amide (1) N-[N'-(2-Chloroethyl)carbamoyl]-L-phenylalanine amide

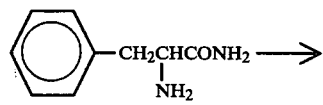

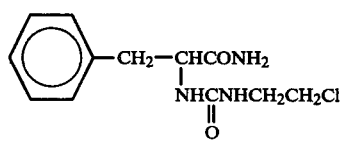

L-Phenylalanine amide (a commercial product available from Sigma Chemical Co.; 400 mg, 2.44 mmol.) was dissolved in methanol (6 ml), to which was then added dropwise 2-chloroethyl isocyanate (0.24 ml, 1.2 moles per mole of the starting compound) at room temperature under stirring and the mixture was held under the same conditions for further 20 minutes to complete the reaction.

The reaction solution was analyzed by TLC with a developer system of chloroform-methanol (7:1 by volume), where it was confirmed that the spot at $R_f$0.21 for the starting compound disappeared and a single spot at $R_f$0.42 for the desired product appeared.

The reaction solution was concentrated in vacuo to leave a white crystalline solid residue which was then washed with isopropanol, affording the titled compound (553 mg).

Yield: 84.1%; m.p. 158°–160° C.; $[\alpha]_D^{22}$+3.0° (c 0.54, methanol);

Elemental analysis: Calculated for $C_{12}H_{16}N_3O_2Cl$, MW=269.729: C, 53.43, H, 5.98, N, 15.58, Cl, 13.15%. Found: C, 53.49, H, 6.02, N, 15.34, Cl, 12.90%.

(2) N-[N'-(2-Chloroethyl)-N'-nitrosocarbamoyl]-L-phenylalanine amide

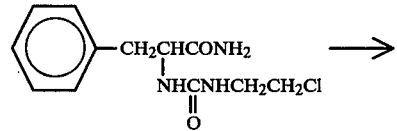

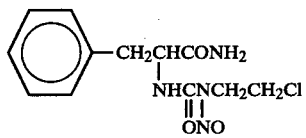

The compound obtained in step (1) above (400 mg, 1.48 mmol.) was dissolved in a 99% formic acid (3 ml), to which was then added sodium nitrite (113 mg, 1.1 moles per mole of the starting compound) over about 5 minutes under stirring and ice-cooling and the reaction mixture was held under the conditions same as above for further 30 minutes to complete the reaction.

The reaction solution was analyzed by TLC with a developer system of chloroform-methanol (9:1 by volume), where it was confirmed that the spot at $R_f$0.33 for the starting compound disappeared and a single spot at $R_f$0.51 for the desired product appeared which showed a UV absorption.

Then, Amberlite IR-120 (H+ form) (5 ml) which was suspended in methanol was added to the reaction solution and the mixture was stirred for 20 minutes. After the resin was removed by filtration, the filtrate was concentrated in vacuo and then azeotropically distilled with ethanol to leave a crystalline solid residue. The residue was washed with ethyl ether, affording the titled compound (310 mg).

Yield: 70.0%; m.p. 113°–115° C. (Dec.); $[\alpha]_D^{22}$−30.6° (c 0.36, DMF);

Elemental analysis: Calculated for $C_{12}H_{15}N_4O_3Cl$, MW=298.729: C, 48.24, H, 5.06, N, 18.76, Cl, 11.87%. Found: C, 47.94, H, 5.01, N, 18.44, Cl, 11.58%.

EXAMPLE 7

Preparation of N-[N'-(2-chloroethyl)-N'-nitrosocarbamoyl]-L-tryosine amide (1) N-[N'-(2-Chloroethyl)carbamoyl]-L-tyrosine amide

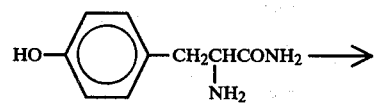

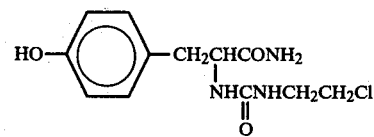

L-Tyrosine amide (a commercial product available from Sigma Co.; 400 mg, 2.22 mmol.) was dissolved in methanol (8 ml), to which was then added dropwise 2-chloroethyl isocyanate (0.22 ml) at room temperature under stirring, during which white crystals were deposited after several minutes from the start of addition. After the lapse of 20 minutes, the supernatant liquid was analyzed by TLC with a developer system of chloroform-methanol (7:1 by volume), where it was confirmed that the spot at $R_f$0.09 for the starting compound disappeared and a single spot at $R_f$0.24 for the desired product appeared.

The white crystalline solid so deposited was filtered and washed with hot methanol to yield a first crop of the titled compound (296 mg). The filtrate was concentrated in vacuo to leave a white solid mass which was washed with hot methanol to yield a second crop of the titled compound (252 mg).

Total yield: 548 mg; Yield: 86.4%; m.p. 187°–189° C. (Dec.); $[\alpha]_D^{22}$+0.4° (c 0.5, DMF):

Elemental analysis: Calculated for $C_{12}H_{16}N_3O_3Cl$, MW=285.729: C, 50.44, H, 5.64, N, 14.71, Cl, 12.41%. Found: C, 50.18, H, 5.68, N, 14.47, Cl, 12.10%.

(2) N-[N'-(2-Chloroethyl)-N'-nitrosocarbamoyl]-L-tyrosine amide

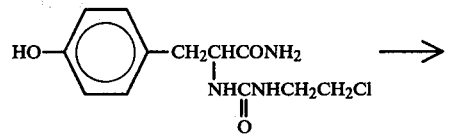

-continued

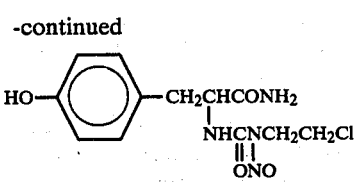

The compound obtained in step (1) above (200 mg, 0.64 mmol.) was dissolved in a 99% formic acid (1.5 ml), to which was then added sodium nitrite (48.6 mg, 1.1 moles per mole of the starting compound) over about 5 minutes under stirring and ice-cooling and the reaction mixture was held under the conditions same as above for further 30 minutes to complete the reaction, during which the mixture was considerably colored with reddish brown.

The reaction solution was analyzed by TLC with a developer system of chloroform-methanol (7:1 by volume), where it was confirmed that the spot at $R_f 0.24$ for the starting compound disappeared and a main spot at $R_f 0.48$ for the desired product having a UV absorption together with a secondary spot at $R_f 0.68$ for a by-product having a UV absorption appeared.

Then, Amberlite IR-120 (H+ form) (5 ml) which was suspended in methanol was added to the reaction solution and the mixture was stirred for 20 minutes to leave a deep reddish brown oily residue. The residue was purified by column chromatography on silica gel (Wako-gel C-300, 10 g) with a developer system of chloroform-methanol (7:1 by volume). Fractions containing the desired object product were collected together, concentrated in vacuo and azeotropically distilled with ethanol to leave a crystalline solid residue. The residue was washed with isopropyl ether, yielding the titled compound (113 mg).

Yield: 51.3%; m.p. 135.5°–137° C. (Dec.); $[\alpha]_D^{22} -30.4°$ (c 0.5, DMF);

Elemental analysis: Calculated for $C_{12}H_{15}N_4O_4Cl$, MW=314.729: C, 45.75, H, 4.80, N, 17.80, Cl, 11.27%. Found: C, 45.53, H, 4.99, N, 17.57, Cl, 11.45%.

EXAMPLE 8

Preparation of N-[N'-(2-chloroethyl)-N'-nitrosocarbamoyl]-L-valine amide (1) N-[N'-(2-Chloroethyl)carbamoyl]-L-valine amide

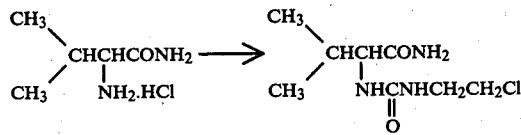

L-Valine amide hydrochloride (a commercial product available from Sigma Co.; 200 mg, 1.31 mmol.) was dissolved in methanol (6 ml), to which was then added Amberlite IRA 400 (OH⁻ form) (4 ml) suspended in methanol and the mixture was stirred for 20 minutes to cause dehydrochlorination.

After the resin was filtered off, the filtrate was concentrated to a volume of about 2 ml, to which was added dropwise 2-chloroethyl isocyanate (0.16 ml, 1.5 moles per mole of the starting compound). After several minutes, white crystals were deposited. After the lapse of 20 minutes, the supernatant liquid was analyzed by TLC with a developer system of chloroform-methanol (5:1 by volume), where it was confirmed that the spot at $R_f 0.36$ for the starting compound disappeared and a single spot at $R_f 0.74$ for the desired product appeared.

The crystals so deposited were collected by filtration and washed with methanol to yield a first crop of the titled compound (135 mg). The filtrate was concentrated in vacuo to leave white crystals, which were recrystallized from methanol to yield a second crop of the titled compound (114 mg).

Total yield: 249 mg; Yield: 85.7%; m.p. 197°–199° C.; $[\alpha]_D^{22} +48.9°$ (c 0.45, DMF);

Elemental analysis: Calculated for $C_8H_{16}N_3O_2Cl$, MW=221.689: C, 43.34, H, 7.28, N, 18.96, Cl, 15.99%. Found: C, 43.29, H, 7.15, N, 18.75, Cl, 16.15%.

(2) N-[N'-(2-Chloroethyl)-N'-nitrosocarbamoyl]-L-valine amide

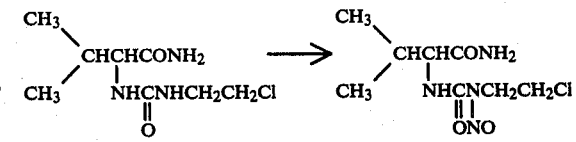

The compound obtained in step (1) above (200 mg, 0.90 mmol.) was dissolved in a 99% formic acid (1.5 ml), to which was then added sodium nitrite (93 mg, 1.5 moles per mole of the starting compound) over about 5 minutes under stirring and ice-cooling and the reaction mixture was held under the conditions same as above for further 30 minutes to complete the reaction.

The reaction solution was analyzed by TLC with a developer system of chloroform-methanol (9:1 by volume), where it was confirmed that the spot at $R_f 0.27$ for the starting compound disappeared and a single spot at $R_f 0.50$ for the desired product appeared which showed a UV absorption.

Then, Amberlite IR-120 (H+ form) (4 ml) which was suspended in methanol was added to the reaction solution and the mixture was stirred for 20 minutes. After the resin was removed by filtration, the filtrate was concentrated in vacuo below 30° C. to leave a pale yellow crystalline solid residue. The residue was washed with ethyl ether, affording the titled compound (181 mg).

Yield: 80.0%; m.p. 115°–117° C. (Dec.); $[\alpha]_D^{22} +60.7°$ (c 0.6, DMF);

Elemental analysis: Calculated for $C_8H_{15}N_4O_3Cl$, MW=250.689: C, 38.33, H, 6.83, N, 22.35, Cl, 14.14%. Found: C, 38.26, H, 6.55, N, 22.53, Cl, 14.35%.

EXAMPLE 9

Preparation of N-[N'-(2-chloroethyl)-N'-nitrosocarbamoyl]-DL-leucine amide (1) N-[N'-(2-Chloroethyl)carbamoyl]-DL-leucine amide

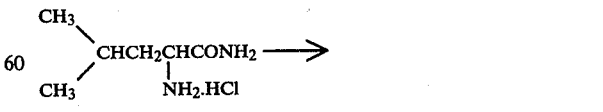

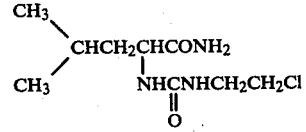

DL-Leucine amide hydrochloride (a commercial product available from Sigma Co.; 200 mg, 1.20 mmol.) was dissolved in methanol (6 ml), to which was then added Amberlite IRA 400 (OH⁻ form) (3.6 ml) suspended in methanol and the mixture was stirred for 20 minutes to cause dehydrochlorination.

After the resin was filtered off, the filtrate was concentrated to a volume of about 2 ml, to which was added dropwise 2-chloroethyl isocyanate (0.16 ml, 1.5 moles per mole of the starting compound) at room temperature under stirring and the mixture was held under the same conditions for further 20 minutes to complete the reaction.

The reaction solution was analyzed by TLC with a developer system of chloroform-methanol (5:1 by volume), where it was confirmed that the spot at $R_f$ 0.25 for the starting compound disappeared and a single spot at $R_f$ 0.57 for the desired product appeared.

The reaction solution was concentrated in vacuo to leave a white crystalline solid residue which was recrystallized from ethanol to yield a first crop (196 mg) and a second crop (33 mg) of the titled compound.

Total yield: 229 mg; Yield: 80.9%; m.p. 156°–158° C.; Elemental analysis: Calculated for $C_9H_{18}N_3O_2Cl$, MW=235.715: C, 45.86, H, 7.70, N, 17.83, Cl, 15.04%. Found: C, 46.05, H, 7.67, N, 17.56, Cl, 15.28%.

(2) N-[N'-(2-Chloroethyl)-N'-nitrosocarbamoyl]-DL-leucine amide

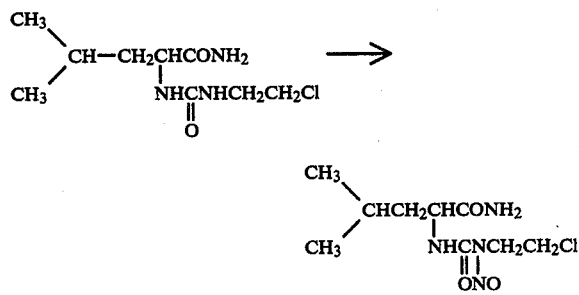

The compound obtained in step (1) above (400 mg, 1.70 mmol.) was dissolved in a 99% formic acid (2.5 ml), to which was then added sodium nitrite (129 mg, 1.1 moles per mole of the starting compound) over about 5 minutes under stirring and ice-cooling and the reaction mixture was held under the same conditions for further 30 minutes to complete the reaction.

The reaction solution was analyzed by TLC with a developer system of chloroform-methanol (9:1 by volume), where it was confirmed that the spot at $R_f$ 0.23 for the starting compound disappeared and a main spot at $R_f$ 0.49 for the desired product having a UV absorption together with a secondary spot at $R_f$ 0.38 for a by-product appeared.

Then, Amberlite IR-120 (H+ form) (6 ml) which was suspended in methanol was added to the reaction solution and the mixture was stirred for 20 minutes. After the resin was removed by filtration, the filtrate was concentrated in vacuo below 30° C. to leave a pale yellow oily residue. The residue was allowed to stand in a desiccator for several days to complete the deposition of crystals. The crystals were washed with isopropyl ether to afford the titled compound (298 mg). (In a second and later operations, the crystallization may be achieved with the addition of seed crystals previously obtained.)

Yield: 66.3%; m.p. 82°–84° C.;
Elemental analysis: Calculated for $C_9H_{17}N_4O_3Cl$, MW=264.715: C, 40.83, H, 6.47, N, 21.17, Cl, 13.39%. Found: C, 40.60, H, 6.43, N, 20.98, Cl, 13.20%.

EXAMPLE 10

Preparation of N-[N'-(2-chloroethyl)-N'-nitrosocarbamoyl]-L-serine amide (1) N-[N'-(2-Chloroethyl)carbamoyl]-L-serine amide

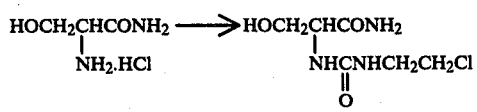

L-Serine amide hydrochloride (a commercial product available from Sigma Co.; 300 mg, 2.13 mmol.) was dissolved in methanol (20 ml), to which was then added Amberlite IRA 400 (OH⁻ form) (6.4 ml) suspended in methanol and the mixture was stirred for 20 minutes to cause dehydrochlorination.

After the resin was filtered off, the filtrate was concentrated to a volume of about 5 ml, to which was added dropwise 2-chloroethyl isocyanate (0.21 ml, 1.2 moles per mole of the starting compound) at room temperature under stirring and the mixture was held under the same conditions for further 20 minutes to complete the reaction.

The reaction solution was analyzed by TLC with a developer system of chloroform-methanol (4:1 by volume), where it was confirmed that the spot at $R_f$ 0.1 for the starting compound disappeared and a single spot at $R_f$ 0.33 for the desired product appeared.

The reaction solution was concentrated in vacuo to leave a white crystalline solid residue which was then washed with isopropanol, affording the titled compound (338 mg).

Yield: 75.6%; m.p. 131°–132° C.; $[\alpha]_D^{22}$+35.7° (c 0.6, methanol);

Elemental analysis: Calculated for $C_6H_{12}N_3O_3Cl$, MW=290.637: C, 34.37, H, 5.77, N, 20.05, Cl, 16.91%. Found: C, 34.14, H, 5.78, N, 19.80, Cl, 17.13%.

(2) N-[N'-(2-Chloroethyl)-N'-nitrosocarbamoyl]-L-serine amide

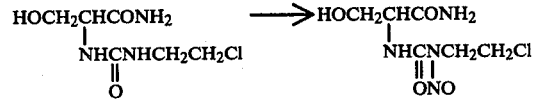

The compound obtained in step (1) above (200 mg, 0.954 mmol.) was dissolved in a 99% formic acid (1.5 ml), to which was then added sodium nitrite (72 mg, 1.1 moles per mole of the starting compound) over about 5 minutes under stirring and ice-cooling and the reaction mixture was held under the same conditions for further 30 minutes to complete the reaction.

The reaction solution was analyzed by TLC with a developer system of chloroform-methanol (7:1 by volume), where it was confirmed that the spot at $R_f$ 0.15 for the starting compound disappeared and a single spot at $R_f$ 0.35 for the desired product having a UV absorption appeared.

Then, Amberlite IR-120 (H+ form) (3 ml) which was suspended in methanol was added to the reaction solution and the mixture was stirred for 20 minutes. After the resin was removed by filtration, the filtrate was concentrated in vacuo at 30° C. and then azeotropically distilled with a mixture of chloroform-methanol (9:1 by volume) to leave a pale yellow crystalline solid residue. The residue was washed with ethyl acetate, affording the titled compound (151 mg).

Yield: 66.3%; m.p. 117°–120° C. (Dec.); $[\alpha]_D^{21} + 57.6°$ (c 0.7, methanol);

Elemental analysis: Calculated for $C_6H_{11}N_4O_4Cl$, MW=238.637: C, 30.20, H, 4.65, N, 23.48, Cl, 14.86%. Found: C, 30.43, H, 4.80, N, 23.25, Cl, 15.05%.

EXAMPLE 11

Preparation of N-[N'-(2-chloroethyl)-N'-nitrosocarbamoyl]-L-methionine amide (1) N-[N'-(2-Chloroethyl)carbamoyl]-L-methionine amide

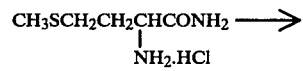

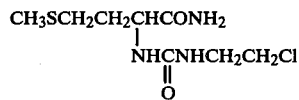

L-Methionine amide hydrochloride (a commercial product available from Sigma Co.; 200 mg, 1.08 mmol.) was dissolved in methanol (6 ml), to which was then added Amberlite IRA 400 (OH⁻ form) (3.2 ml) suspended in methanol, and the mixture was stirred for 20 minutes to cause dehydrochlorination.

After the resin was filtered off, the filtrate was concentrated to a volume of about 3 ml, to which was added dropwise 2-chloroethyl isocyanate (0.11 ml, 1.2 moles per mole of the starting compound) at room temperature under stirring and the mixture was held under the same conditions for further 20 minutes to complete the reaction.

The reaction solution was analyzed by TLC with a developer system of chloroform-methanol (5:1 by volume), where it was confirmed that the spot at $R_f$0.28 for the starting compound disappeared and a single spot at $R_f$0.58 for the desired product appeared.

The reaction solution was concentrated in vacuo to leave a white crystalline solid residue. The residue was recrystallized from ethanol to yield a first crop (198 mg) and a second crop (39 mg) of the titled compound.

Total yield: 237 mg; Yield: 86.2%; m.p. 150°–151° C.; $[\alpha]_D^{22} + 5.2°$ (c 0.42, methanol);

Elemental analysis: Calculated for $C_8H_{16}N_3O_2ClS$, MW=253.749: C, 37.86, H, 6.36, N, 16.56%. Found: C, 37.71, H, 6.18, N, 16.33%.

(2) N-[N'-(2-Chloroethyl)-N'-nitrosocarbamoyl]-L-methionine amide

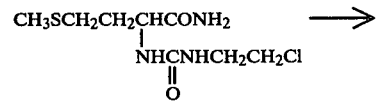

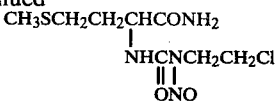

The compound obtained in step (1) above (700 mg, 2.76 mmol.) was dissolved in a 99% formic acid (6 ml), to which was then added sodium nitrite (210 mg, 1.1 moles per mole of the starting compound) over about 5 minutes under stirring and ice-cooling and the reaction mixture was held under the same conditions for further 30 minutes to complete the reaction.

The reaction solution was analyzed by TLC with a developer system of chloroform-methanol (9:1 by volume), where it was confirmed that the spot at $R_f$0.33 for the starting compound disappeared and a main spot at $R_f$0.65 for the desired product having a UV absorption together with a secondary spot at $R_f$0.51 for a by-product appeared.

Then, Amberlite IR-120 (H+ form) (9 ml) which was suspended in methanol was added to the reaction solution (which was slightly colored with brown) and the mixture was stirred for 20 minutes. After the resin was removed by filtration, the filtrate was concentrated in vacuo at 30° C. or lower and then azeotropically distilled with a mixture of methanol and isopropyl ether to leave a crystalline solid residue. The residue was washed with ethyl ether, affording the titled compound (555 mg).

Yield: 71.2%; m.p. 95°–97° C.; $[\alpha]_D^{22} + 18.7°$ (c 0.45, DMF);

Elemental analysis: Calculated for $C_8H_{15}N_4O_3ClS$, MW=282.749: C, 33.98, H, 5.35, N, 19.82%. Found: C, 34.27, H, 5.40, N, 19.63%.

What I claim is:

1. A nitrosourea derivative of the following formula (I):

wherein R represents hydrogen or methyl.

2. A nitrosourea derivative as claimed in claim 1 selected from the group consisting of N-[N'-(2-chloroethyl)-N'nitrosocarboamoyl]glycine amide and N-[N'-(2-chloroethyl)-N'-nitrosocarbamoyl]sarcosine amide.

3. A pharmaceutical composition comprising an effective tumor-inhibiting amount of a nitrosourea derivative of the following formula (I):

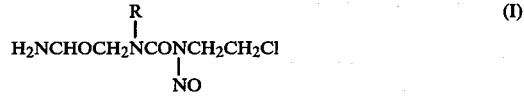

wherein R represents hydrogen or methyl and a pharmaceutically acceptable excipient, carrier or diluent.

4. A method for the therapeutic treatment of tumors in animals which comprises administering to said animals a tumor-inhibiting amount, of a nitrosourea derivative of formula (I):

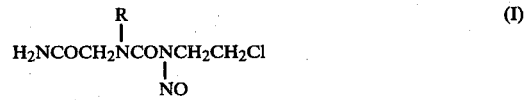

wherein R represents hydrogen or methyl.

* * * * *